United States Patent
Nonaka et al.

(10) Patent No.: US 10,590,442 B2
(45) Date of Patent: Mar. 17, 2020

(54) METHOD FOR PRODUCING C4 DICARBOXYLIC ACID

(71) Applicant: Kao Corporation, Chuo-ku, Tokyo (JP)

(72) Inventors: Kyoshiro Nonaka, Wakayama (JP); Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/313,547

(22) PCT Filed: Jun. 22, 2017

(86) PCT No.: PCT/JP2017/022943
§ 371 (c)(1),
(2) Date: Dec. 27, 2018

(87) PCT Pub. No.: WO2018/003641
PCT Pub. Date: Jan. 4, 2018

(65) Prior Publication Data
US 2019/0316159 A1    Oct. 17, 2019

(30) Foreign Application Priority Data

Jun. 29, 2016 (JP) ................................ 2016-129167

(51) Int. Cl.
*C12P 7/46* (2006.01)
*C12N 1/14* (2006.01)

(52) U.S. Cl.
CPC . *C12P 7/46* (2013.01); *C12N 1/14* (2013.01)

(58) Field of Classification Search
CPC ..................................... C12P 7/46; C12N 1/14
See application file for complete search history.

(56) References Cited

U.S. PATENT DOCUMENTS

| | | |
|---|---|---|
| 2010/0009419 A1 | 1/2010 | Burk et al. |
| 2013/0059353 A1 | 3/2013 | McFarland et al. |
| 2015/0104543 A1 | 4/2015 | Winkler et al. |
| 2015/0176038 A1 | 6/2015 | Rush et al. |
| 2018/0291406 A1 | 10/2018 | Kaneda |
| 2018/0327791 A1 | 11/2018 | Kaneda |

FOREIGN PATENT DOCUMENTS

| | | |
|---|---|---|
| CN | 103013843 A | 4/2013 |
| JP | 2018-088860 A | 6/2018 |
| WO | WO 2009/011974 A1 | 1/2009 |
| WO | WO 2009/155382 A1 | 12/2009 |
| WO | WO 2010/111344 A2 | 9/2010 |
| WO | WO 2013/028512 A1 | 2/2013 |
| WO | WO 2014/018755 A1 | 1/2014 |
| WO | WO 2016/106367 A1 | 6/2016 |
| WO | WO 2017/065167 A1 | 4/2017 |
| WO | WO 2017/073640 A1 | 5/2017 |

OTHER PUBLICATIONS

International Search Report (ISR) for PCT/JP2017/022943; I.A. fd: Jun. 22, 2017, dated Sep. 5, 2017 from the Japan Patent Office, Tokyo, Japan.
International Preliminary Report on Patentability (IPRP), Chapter I of the Patent Cooperation Treaty, including the Written Opinion for PCT/JP2017/022943; I.A. fd: Jun. 22, 2017, dated Jan. 1, 2019, by the International Bureau of WIPO, Geneva, Switzerland.
Zhang, B et al., "Metabolic engineering of *Rhizopus oryzae*: effects of overexpressing *pyc* and *pepc* genes on fumaric acid biosynthesis from glucose," Metab Eng. Sep. 2012;14(5):512-20. doi: 10.1016/j.ymben.2012.07.001. Epub Jul. 17, 2012.
ROE00000398 Rhizopus oryzae Company Rhizopus oryzae cDNA, mRNA sequence, Database GenBank [online] Accession No. EE009190, Jul. 18, 2006, <URL: https://www.ncbi.nlm.nih.gov/nucest/110467151> [retrieved on Aug. 18, 2017].
Hypothetical protein RO3G_10751, [Rhizopus delemar RA 99-880], Database GenBank [online], Accession No. EIE86040, Mar. 23, 2015, <URL: https://www.ncbi.nlm.nih.gov/protein/384495549> [retrieved on Aug. 23, 2017].
Rhizopus oryzae RA 99-880 supercont3.8 genomic scaffold, whole genome shotgun sequence, Database GenBank [online] Accession No. CH476739, Mar. 23, 2015, URL:https://www.ncbi.nlm/nih/gov/nucore/CH476739> [retrieved on Aug. 23, 2017].
Ma, LJ et al., "Genomic analysis of the basal lineage fungus *Rhizopus oryzae* reveals a whole-genome duplication," PLoS Genet. Jul. 2009;5(7):e1000549. doi: 10.1371/journal.pgen.1000549. Epub Jul. 3, 2009, 11 pages.
Zhang, B et al., "Metabolic engineering of *Rhizopus oryzae*: Effects of overexpressing *fumR* gene on cell growth and fumaric acid biosynthesis from glucose," Process Biochemistry 47(12), Dec. 2012, doi.org/10.1016/j.procbio.2012.08.009, Available online Aug. 17, 2012.
Hewett-Emmitt, D et al., "Functional diversity, conservation, and convergence in the evolution of the α-, β-, and γ-carbonic anhydrase gene families," Mol Phylogenet Evol. Feb. 1996;5(1):50-77.
Park, JY et al., "$CO_2$ reduction and organic compounds production by photosynthetic bacteria with surface displayed carbonic anhydrase and inducible expression of phosphoenolpyruvate carboxylase," Enzyme Microb Technol. Jan. 2017;96:103-110. doi: 10.1016/j.enzmictec.2016.10.005. Epub Oct. 13, 2016.

*Primary Examiner* — Karen Cochrane Carlson
(74) *Attorney, Agent, or Firm* — Sterne, Kessler, Goldstein & Fox P.L.L.C.

(57) ABSTRACT

Improvement in C4 dicarboxylic acid productivity in a host cell is provided. A polypeptide consisting of the amino acid sequence represented by SEQ ID NO: 2 or an amino acid sequence having at least 90% identity therewith.

20 Claims, No Drawings
Specification includes a Sequence Listing.

METHOD FOR PRODUCING C4 DICARBOXYLIC ACID

FIELD OF THE INVENTION

The present invention relates to biological production of C4 dicarboxylic acids.

BACKGROUND OF THE INVENTION

C4 dicarboxylic acids are utilized not only in various applications in the food industry as an acidulant, an antimicrobial agent and a pH adjusting agent, but also used as a raw material for synthetic resins and biodegradable polymers. Thus, C4 dicarboxylic acids are industrially valuable substances. C4 dicarboxylic acids are industrially produced by either chemical synthesis from petrochemical raw materials or microbial fermentation. Previously, C4 dicarboxylic acids have been mainly produced by chemical synthesis due to a lower cost. However, from the viewpoint of rising costs of the raw materials, the burden on the environment, and the like, production methods by microbial fermentation using a recyclable resource as a raw material have recently been attracting attention.

It is known that fumaric acid, which is one of C4 dicarboxylic acids, can be produced by using a fermentative fungus, such as *Rhizopus*. *Rhizopus* produces fumaric acid using glucose as a carbon source, and excretes the produced fumaric acid to the outside of the cell. To date, as techniques for producing fumaric acid with high productivity by using *Rhizopus*, improvements of culturing methods, and preparations of strains having high productivity by mutation breeding are known. However, since the genetic background of *Rhizopus* has not yet been well studied, the development of the techniques for producing fumaric acid with high productivity by *Rhizopus* through gene recombination is not easy and has little information. There are only a few reports for improving fumaric acid productivity by introducing a gene encoding pyruvate carboxylase from *Saccharomyces cerevisiae* into *Rhizopus delemar* (Patent Literature 1), or by introducing a gene encoding phosphoenolpyruvate carboxylase from *E. coli* into *Rhizopus oryzae* (Non Patent Literature 1).

(Patent Literature 1) CN-A-103013843
(Non Patent Literature 1) Metabolic Engineering, 2012, 14: 512-520

SUMMARY OF THE INVENTION

The present invention provides a polypeptide consisting of an amino acid sequence represented by SEQ ID NO: 2 or an amino acid sequence having at least 90% identity therewith.

The present invention also provides a polynucleotide encoding the aforesaid polypeptide.

The present invention also provides a vector or DNA fragment comprising the aforesaid polynucleotide.

The present invention also provides a transformed cell comprising the aforesaid polynucleotide or the aforesaid vector or DNA fragment.

Further the present invention provides a method for producing a C4 dicarboxylic acid, comprising culturing the aforesaid transformed cell.

Further the present invention provides a method for producing a transformed cell, comprising introducing the aforesaid polynucleotide or the aforesaid vector into a host cell.

Further the present invention provides a method for improving C4 dicarboxylic acid productivity in a host cell, comprising introducing the aforesaid polynucleotide or the aforesaid vector or DNA fragment into the host cell, or enhancing expression of the aforesaid polynucleotide.

DETAILED DESCRIPTION OF THE INVENTION

The present invention relates to a polypeptide having an effect of improving C4 dicarboxylic acid productivity in a host cell, a gene encoding the polypeptide, a transformed cell comprising the gene, and a method for producing C4 dicarboxylic acids using the transformed cell.

The present inventors have conducted intensive studies, and found that the cell in which expression of a polypeptide consisting of the amino acid sequence represented by SEQ ID NO: 2 has been enhanced has improved C4 dicarboxylic acid productivity.

The polypeptide of the present invention has the function of improving C4 dicarboxylic acid productivity in a cell. The cell in which expression of the polypeptide of the present invention is enhanced (for example, the cell into which the gene encoding the polypeptide is introduced) can produce C4 dicarboxylic acids more rapidly. Therefore, the polypeptide of the present invention and the cell in which expression of the polypeptide is enhanced are useful for biological production of C4 dicarboxylic acids. These and other features and advantages of the present invention will become more apparent from the following description of the present specification.

1. Definition

As used herein, the identity of amino acid sequences or nucleotide sequences is calculated by Lipman-Pearson method (Science, 1985, 227: 1435-1441). Specifically, the identity of amino acid sequences or nucleotide sequences is calculated by using amino acid sequence×amino acid sequence maximum matching or nucleotide sequence× nucleotide sequence maximum matching of homology analysis program of genetic information processing software GENETYCS Ver.12 and performing analysis with Match of −1, Mismatch of 1, Gap of 1, and *N+2.

As used herein, the identity of amino acid or nucleotide sequences refers to the ratio (%) of the number of positions where identical amino acids or nucleotides are present in two amino acid sequences or two nucleotide sequences based on the number of amino acids or nucleotides of full-length sequence when the two amino acid sequences or two nucleotide sequences are aligned (in alignment) so that the two sequences match at maximum. The identity is distinct from homology which is calculated including both similarity and identity wherein a group of similar amino acids or nucleotides is considered to have a similarity.

As used herein, "at least 90% identity" with respect to amino acid sequences or nucleotide sequences refers to identity of 90% or more, preferably 95% or more, more preferably 96% or more, further preferably 97% or more, further preferably 98% or more, further preferably 99% or more.

As used herein, "corresponding region" on an amino acid sequence or a nucleotide sequence can be determined by aligning a target sequence and a reference sequence (for example, the amino acid sequence represented by SEQ ID NO: 2) so as to have maximum homology. Alignment of amino acid sequences or nucleotide sequences can be performed using known algorithms, and procedures therefor are known to those skilled in the art. For example, alignment can be made manually based on the above-mentioned Lipman-Pearson method or the like, and also be made by using Clustal W multiple alignment program (Thompson, J. D. et al, 1994, Nucleic Acids Res. 22: 4673-4680) at default setting. Clustal W can be available on websites such as a website of the European Bioinformatics Institute: EBI [www.ebi.ac.uk/index.html]) or a website of the DNA Data Bank of Japan (DDBJ) [www.ddbj.nig.ac.jp/Welcome-j.html]) which is operated by the National Institute of Genetics. A region of a target sequence aligned with a certain region of a reference sequence by the above-described alignment operation is considered as "corresponding region" to the certain region.

As used herein, an "amino acid sequence in which one or more amino acids are deleted, substituted, added or inserted" refers to an amino acid sequence in which 1 or more and 10 or less, preferably 1 or more and 8 or less, more preferably 1 or more and 5 or less, further preferably 1 or more and 3 or less amino acids are deleted, substituted, added or inserted. Also as used herein, a "nucleotide sequence in which one or more nucleotides are deleted, substituted, added or inserted" refers to a nucleotide sequence in which 1 or more and 30 or less, preferably 1 or more and 24 or less, more preferably 1 or more and 15 or less, further preferably 1 or more and 9 or less nucleotides are deleted, substituted, added or inserted. As used herein, the "addition" of an amino acid(s) or a nucleotide(s) includes addition of the amino acid(s) or the nucleotide(s) to one end or both ends of the sequence.

As used herein, "upstream" and "downstream" with respect to a gene refers to the upstream and downstream of the gene in transcription direction. For example, a "gene arranged downstream of a promoter" means that the gene exists at the 3'side of the promoter in the DNA sense strand, and upstream of a gene refers to the region of the 5'side of the gene in the DNA sense strand.

As used herein, "operably link" between a gene and a control region refers to that the gene is linked to the control region so that the gene can be expressed under the control of the control region. The procedure of making "operably link" between a gene and a control region is well known in the art.

As used herein, the term "instrinsic" with respect to a function, property or a trait of a cell means that the function, property or trait is present in the wild-type of the cell. In contrast, the term "exogenous" is used to represent that the function, property or trait has been introduced from outside, not originally present in the cell. For example, the "exogenous" gene or polynucleotide is a gene or polynucleotide introduced into the cell from the outside. The exogenous gene or polynucleotide may be derived from a homogenous biological species of the cell into which the gene or polynucleotide are introduced or may be derived from a different biological species (i.e., a heterologous gene or polynucleotide).

As used herein, "C4 dicarboxylic acid productivity" of a cell is represented as the production speed of C4 dicarboxylic acids in a culture medium of the cell. More specifically, "C4 dicarboxylic acid productivity" is represented as a value (g/L/h) obtained by dividing the mass of C4 dicarboxylic acids produced by the cell during a certain culturing time elapsed after the start of culturing per a medium volume by a culturing time. The amount of C4 dicarboxylic acids produced by the cell can be calculated as the amount of C4 dicarboxylic acids in the culture supernatant obtained by removing cells from the cultured broth of the cells. The amount of C4 dicarboxylic acids in the culture supernatant can be measured by high performance liquid chromatography (HPLC) or the like. More specific measurement procedure is exemplified in Reference Example 1 described below.

As used herein, "improvement in C4 dicarboxylic acid productivity" in a transformed cell means that the transformed cell has improved C4 dicarboxylic acid productivity as compared to a host cell or control cell. Improvement rate of C4 dicarboxylic acid productivity in a transformed cell is calculated by the following equation.

Improvement rate (%)=(C4 dicarboxylic acid productivity in transformed cell/C4 dicarboxylic acid productivity in host cell or control cell)× 100-100

As used herein, a transformed cell means a cell in which expression of the polypeptide of the present invention is enhanced, for example, a cell obtained by introducing the polynucleotide encoding the polypeptide of the present invention into a host cell so as to allow the expression, or a cell in which expression of the polynucleotide is enhanced (i.e., transcription amount thereof is improved). Herein, a "host cell" refers to a host cell (parent cell) of the transformed cell. Also a "control cell" refers to a cell into which a vector not containing the polynucleotide encoding the polypeptide of the present invention is introduced. The control cell is used as a comparison to the transformed cell into which a vector containing the polynucleotide is introduced. Preferably, the improvement rate of C4 dicarboxylic acid productivity is calculated based on the C4 dicarboxylic acid productivity of each cell at the time when the production speed of C4 dicarboxylic acids by the transformed cell reaches maximum. Accordingly, as used herein, "a transformed cell in which C4 dicarboxylic acid productivity is improved by X % or more" refers to a transfo med cell in which the improvement rate of C4 dicarboxylic acid productivity calculated by the above equation is X % or more. Further, as used herein, "X % or more improvement in C4 dicarboxylic acid productivity" of the cell means that improvement rate of C4 dicarboxylic acid productivity of the cell calculated by the above equation is X % or more.

Examples of the C4 dicarboxylic acids produced in the present invention include fumaric acid, malic acid and succinic acid, preferably fumaric acid and malic acid, more preferably fumaric acid.

As used herein, a "carbonic anhydrase" means an enzyme (EC 4.2.1.1) having catalytic activity for promoting either or both of the reaction producing carbonate ion ($HCO_3^-$) from carbon dioxide molecule ($CO_2$) and water molecule ($H_2O$) in aqueous solution and the reverse reaction thereof. Further, "carbonic anhydrase activity" refers to the catalytic activity of carbonic anhydrase, and can be determined, for example, by the known method (C. S. Gai et al., AMB Express 2014, 4, 2-13) or the like.

2. Improvement in C4 Dicarboxylic Acid Productivity in Cell (2.1. Novel Polypeptide)

In one embodiment, the present invention provides a polypeptide consisting of the amino acid sequence represented by SEQ ID NO: 2 or an amino acid sequence having at least 90% identity therewith.

According to search results with polypeptide database (e.g. ncbi Non-Redundant protein sequences (nr)), a protein of unknown function derived from *Lichtheimia ramosa* strain (accession number: LRAMOSA05249) has been found as the most identical known protein with the polypeptide consisting of the amino acid sequence represented by SEQ NO: 2. The sequence identity thereof was 62.77%. Further, the polypeptide consisting of the amino acid sequence represented by SEQ NO: 2 has a region corresponding to positions 152-375 in the protein of unknown function consisting of the amino acid sequence represented by SEQ ID NO: 23 derived from *Rhizopus delemar* RA 99-880 strain (accession number: RO3G_10751). In other words, the polypeptide consisting of the amino acid sequence represented by SEQ NO: 2 is one in which amino acids at the N-terminal side (a sequence of amino acids at positions 2 to 151) have been deleted from the polypeptide consisting of the amino acid sequence represented by SEQ ID NO: 23. It has been found that the sequence identity of the polypeptide with the protein of unknown function is 60.00%, and the polypeptide is different from the protein of unknown function. From the above, the polypeptide has been determined to be a novel polypeptide that is unknown so far, and as described in Examples below, it has been confirmed that the polypeptide has carbonic anhydrase activity. Further, as shown in Examples below, in strains in which expression of the protein of unknown function consisting of the amino acid sequence represented by SEQ ID NO: 23 was enhanced, no improvement in fumaric acid productivity was observed. On the other hand, improvement in fumaric acid productivity was only observed in strains in which expression of the polypeptide consisting of the amino acid sequence represented by SEQ NO: 2 was enhanced.

Accordingly, in a preferred embodiment, the polypeptide of the present invention is a polypeptide consisting of the amino acid sequence represented by SEQ ID NO: 2 or an amino acid sequence having at least 90% identity therewith and having carbonic anhydrase activity.

Examples of the amino acid sequence having at least 90% identity with the amino acid sequence represented by SEQ ID NO: 2 include an amino acid sequence in which one or more amino acids are deleted, substituted, added or inserted in the amino acid sequence represented by SEQ ID NO: 2.

Examples of a method for introducing a mutation such as deletion, substitution, addition, or insertion of an amino acid(s) into an amino acid sequence include a method for introducing a mutation such as deletion, substitution, addition, or insertion of a nucleotide(s) in the nucleotide sequence encoding the amino acid sequence. Examples of the method for introducing a mutation into a nucleotide sequence include mutagenesis using chemical mutagens such as ethyl methanesulfonate, N-methyl-N-nitrosoguanidine and nitrous acid, or physical mutagens such as UV, X-ray, gamma ray and ion beam, a site-directed mutagenesis method, and a method described in Dieffenbach et al (Cold Spring Harbor Laboratory Press, New York, 581-621, 1995). Examples of the site-directed mutagenesis method include a method using Splicing overlap extension (SOE) PCR (Horton et al., Gene 77, 61-68, 1989), ODA method (Hashimoto-Gotoh et al., Gene, 152, 271-276, 1995), and Kunkel method (Kunkel, T. A., Proc. Natl. Acad. Sci. USA, 1985, 82, 488). Alternatively, commercially available site-directed mutagenesis kits such as Site-Directed Mutagenesis System Mutan-SuperExpress Km kit (Takara Bio Inc.), Transformer™ Site-Directed Mutagenesis kit (Clontech Laboratories, Inc.), and KOD-Plus-Mutagenesis kit (TOYOBO CO., LTD.) may be used.

(2.2. Gene, Vector and Transformed Cell)

In another embodiment, the present invention provides a polynucleotide encoding the aforementioned polypeptide of the present invention. In a preferred embodiment, the polynucleotide of the present invention includes a polynucleotide consisting of the nucleotide sequence represented by SEQ ID NO: 1 or a polynucleotide consisting of a nucleotide sequence having at least 90% identity with the nucleotide sequence represented by SEQ ID NO: 1. In a preferred embodiment, the polynucleotide of the present invention encodes a polypeptide consisting of the amino acid sequence represented by SEQ ID NO: 2 or a polypeptide consisting of an amino acid sequence having at least 90% identity therewith and having carbonic anhydrase activity.

Examples of the nucleotide sequence having at least 90% identity with the nucleotide sequence represented by SEQ ID NO: 1 include a nucleotide sequence in which one or more nucleotides are deleted, substituted, added or inserted in the nucleotide sequence represented by SEQ ID NO: 1. The method for introducing a mutation such as deletion, substitution, addition, or insertion of a nucleotide(s) into a nucleotide sequence is as described above. The polynucleotide of the present invention may be in the form of single-stranded or double-stranded, and may be DNA or RNA. The DNA may be cDNA or an artificial DNA such as a chemical synthesized DNA.

The polynucleotide of the present invention may be incorporated into a vector. Preferably, the vector containing the polynucleotide of the present invention is an expression vector. Preferably, the vector is an expression vector capable of introducing the polynucleotide of the present invention into a host cell and expressing the polynucleotide in the host cell. Preferably, the vector includes the polynucleotide of the present invention and a control region operably linked to the polynucleotide. The vector may be a vector capable of extrachromosomally and autonomously growing and replicating, such as a plasmid, or may be a vector to be incorporated intrachromosomally.

Specific examples of the vector include pBluescript II SK(−) (Stratagene), pUC vector (Takara Bio Inc.) such as pUC18/19 and pUC118/119, pET vector (Takara Bio Inc.), pGEX vector (GE healthcare), pCold vector (Takara Bio Inc.), pHY300PLK (Takara Bio Inc.), pUB110 (Mckenzie, T. et al., 1986, Plasmid 15(2): 93-103), pBR322 (Takara Bio Inc.), pRS403 (Stratagene), pMW218/219 (NIPPON GENE CO., LTD.), pRI vector (Takara Bio Inc.) such as pRI909/910, pBI vector (Clontech Laboratories, Inc.), IN3 vector (Inplanta Innovations Inc.), pPTRl/2 (Takara Bio Inc.), pDJB2 (D. J. Ballance et al., Gene, 36, 321-331, 1985), pAB4-1 (van Hartingsveldt W et al., Mol Gen Genet, 206, 71-75, 1987), pLeu4 (M. I. G. Roncero et al., Gene, 84, 335-343, 1989), pPyr225 (C. D. Skory et al., Mol Genet Genomics, 268, 397-406, 2002), and pFG1 (Gruber, F. et al., Curr Genet, 18, 447-451, 1990).

Alternatively, a DNA fragment containing the polynucleotide of the present invention may be constructed. Examples of the DNA fragment include a PCR amplified DNA frayment and a restriction enzyme-cleaved DNA fragment. Preferably, the DNA fragment may be an expression cassette containing the polynucleotide of the present invention and a control region operably linked to the polynucleotide.

The control region contained in the vector or DNA fragment is a sequence for expressing the polynucleotide of the present invention in a host cell into which the vector or DNA fragment has been introduced, and examples of the control region include an expression control region such as a promoter and a terminator, and a replicator. The type of the control region can be selected appropriately depending on the type of a host cell into which the vector or DNA fragment is introduced. As necessary, the vector or DNA fragment may further contain a selection marker such as an antibiotic resistance gene and an amino acid synthesis-related gene.

The transformed cell of the present invention includes a cell in which a polynucleotide encoding the polypeptide of the present invention is introduced into a host cell so as to allow expression and a cell in which expression of the polynucleotide is enhanced. It is preferred that the transformed cell contains an exogenous polynucleotide.

Examples of techniques for introducing the polynucleotide to allow expression or for enhancing expression of the polynucleotide include a technique for introducing a vector or DNA fragment which contains the polynucleotide of the present invention operably linked to a control region, preferably an enhanced control region (a control region which can enhance expression of the polynucleotide compared to that of wild-type) into a host cell, and a technique for arranging an enhanced control region so as to operably link to the polynucleotide of the present invention in the genome of a host cell (for example, replacing a control region sequence of the polynucleotide of the present invention in the genome of the parent cell with an enhanced control region).

The transformed cell of the present invention has preferably 1.1 folds or more, more preferably 2 folds or more, further preferably 5 folds or more, further preferably 10 folds or more, further preferably 15 folds or more, further preferably 20 folds or more improved carbonic anhydrase activity in the cell, as compared to that of the host cell (parent cell). When the host cell does not contain a gene encoding the polypeptide of the present invention and does not express the polypeptide of the present invention, the transformed cell of the present invention include a cell in which a trait is changed so that transcription of the gene is allowed.

The host cell of the transfoLmed cell may be any cell of microorganism, plant and animal. From the viewpoint of production efficiency of C4 dicarboxylic acids, it is preferred that the host cell is a cell of microorganism. The microorganism may be either prokaryotes or eukaryotes. Of these, from the viewpoint of C4 dicarboxylic acid productivity, the microorganism is preferably a filamentous fungus or a yeast, more preferably a filamentous fungus. As the filamentous fungus, any fungi in the filamentous form belonging to the subdivisions, Eumycota and Oomycota are included (as defined in Hawksworth et al., In, Ainsworth and Bisby's Dictionary of The Fungi, 8th edition, 1995, CAB International, bUniversity, Press, Cambridge, UK). A filamentous fungus is generally characterized by mycelial cell wall composed of chitin, cellulose, glucan, chitosan, mannan, and other complex polysaccharide. Vegetative growth thereof is through hyphal extension, and carbon metabolism thereof is obligate aerobic metabolism.

Preferred examples of the filamentous fungus which is used as a host cell of the transformed cell in the present invention include filamentous fungi of the genus *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Parasitella, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma*. Of these, from the viewpoint of C4 dicarboxylic acid productivity, filamentous fungi of the genus *Rhizopus* such as *Rhizopus delemar, Rhizopus arrhizus, Rhizopus chinensis, Rhizopus nigricans, Rhizopus tonkinensis, Rhizopus tritici,* and *Rhizopus oryzae* are preferred, *Rhizopus delemar* and *Rhizopus oryzae* are more preferred, and *Rhizopus delemar* is further preferred.

To introduce the vector or DNA fragment into the host cell, general transformation methods such as an electroporation method, a transformation method, a transfection method, a conjugation method, a protoplast method, a particle gun method, a *Agrobacterium* method can be used.

The transformed cell into which the vector or DNA fragment of interest has been introduced can be selected using a selection marker. For example, when the selection marker is an antibiotic resistance gene, the transformed cell into which the vector or DNA fragment of interest has been introduced can be selected by culturing the cell in a medium containing the antibiotic. As another example, when the selection marker is an amino acid synthesis-related gene, the transformed cell into which the vector or DNA fragment of interest has been introduced can be selected by introducing the gene into a host cell having amino acid auxotrophy, and using the presence or absence of amino acid auxotrophy as an indicator. Alternatively, introduction of the vector or DNA fragment of interest can also be confirmed by examining the DNA sequence of the transformed cell by PCR or the like.

Examples of the enhanced control region include, but are not limited to, a control region of rRNA operon, a control region of a gene encoding ribosomal protein (for example, rp1S gene), adh1 promoter (Japanese Patent Application No. 2015-155759), ldhA promoter (U.S. Pat. No. 6,268,189) pgk1 promoter (WO-A-2001/73083), pgk2 promoter (WO-A-2001/72967), pdcA promoter and amyA promoter (Archives of Microbiology, 2006, 186: 41-50), and tef and 18S rRNA promoter (US-A-2010/112651).

Examples of the method for replacing a control region of the polynucleotide of the present invention present in the genome of the parent cell with an enhanced control region include a method including introducing a DNA fragment containing the enhanced control region and a polynucleotide sequence of selection marker into a host cell, and selecting the cell which is transformed by homologous or non-homologous recombination or the like.

(2.3. Improvement in C4 Dicarboxylic Acid Productivity)

In the transformed cell of the present invention, the expression amount of the polypeptide of the present invention is increased and the carbonic anhydrase activity in the cell is enhanced. Thus, the transformed cell has improved C4 dicarboxylic acid productivity. For example, compared to the host cell (parent cell), the transformed cell containing a vector or DNA fragment containing the polynucleotide is improved in C4 dicarboxylic acid productivity by preferably 5% or more, more preferably 10% or more, further preferably 15% or more.

3. Production of C4 Dicarboxylic Acid

The transformed cell of the present invention has an improved C4 dicarboxylic acid productivity. Therefore, the present invention also provides a method for producing a C4 dicarboxylic acid, including culturing the transformed cell of the present invention. The C4 dicarboxylic acid produced by the production method of the present invention includes fumaric acid, malic acid, and succinic acid, and preferably the C4 dicarboxylic acid is fumaric acid and malic acid, more preferably fumaric acid.

Cultivation of transformed cell in the production method of the present invention includes culturing a microorganism, a plant, an animal, or a cell or tissue thereof which contains the transformed cell. The medium and culture conditions for culturing the transformed cell can be appropriately selected depending on the type of the host of the transformed cell. In general, the medium and culture conditions generally used for culturing the host of the transformed cell can be used.

For example, when the transformed cell is a filamentous fungal cell, the culture temperature may be, for example, from 10° C. to 50° C., preferably from 25° C. to 45° C., and the culture period is not particularly limited as long as C4 dicarboxylic acid of interest is sufficiently produced, but may be for example from 1 to 240 hours, preferably from 12 to 120 hours, preferably from 24 to 72 hours. It is preferably cultured under stirring or aeration.

The medium for culturing a filamentous fungus may be any medium commonly used. Preferably, the medium is a liquid medium, and the medium may be any one of a synthetic medium, a natural medium, and a semi-synthetic medium obtained by supplementing natural ingredients to a synthetic medium. The medium may be commercially available PDB medium (potato dextrose medium; manufactured by Becton, Dickinson and Company, or the like), PDA medium (manufactured by Becton, Dickinson and Company, or the like), LB medium (Luria-Bertani medium; manufactured by NIHON PHARMACEUTICAL CO., LTD (under trade name "Daigo"), or the like), NB medium (Nutrient Broth; manufactured by Becton, Dickinson and Company, or the like), SB medium (Sabouraud medium; manufactured by Oxoid Limited, or the like), SD medium (Synthetic Dropout Broth; for example, from Clontech Laboratories, Inc.) and the like. Generally, the medium contains a carbon source, a nitrogen source, an inorganic salt and the like, however components and composition of the medium can be selected appropriately.

Hereinafter, the preferred medium composition for culturing a filamentous fungus will be described in detail. The concentration of each component in the medium described below represents an initial concentration (at the preparation of medium or at the start of culturing).

Examples of the carbon source in the medium include glucose, maltose, starch hydrolysate, fructose, xylose and sucrose, and among these glucose and fructose are preferred. These saccharides may be used alone or in combination of two or more. The concentration of the carbon source in the medium is preferably 1% (w/v) or more, more preferably 5% (w/v) or more, and is preferably 40% (w/v) or less, more preferably 30% (w/v) or less. Alternatively, the concentration of the carbon source in the medium is preferably from 1 to 40% (w/v), more preferably from 5 to 30% (w/v).

Examples of the nitrogen source in the medium include nitrogen-containing compounds such as ammonium sulfate, urea, ammonium nitrate, potassium nitrate, and sodium nitrate. The concentration of nitrogen source in the medium may be preferably from 0.001 to 0.5% (w/v), more preferably from 0.001 to 0.2% (w/v).

The medium may contain a sulfate, magnesium salt, and zinc salt. Examples of the sulfate include magnesium sulfate, zinc sulfate, potassium sulfate, sodium sulfate, and ammonium sulfate. Examples of the magnesium salt include magnesium sulfate, magnesium nitrate, and magnesium chloride. Examples of the zinc salt include zinc sulfate, zinc nitrate, and zinc chloride. The concentration of the sulfate in the medium is preferably from 0.01 to 0.5% (w/v), more preferably from 0.02 to 0.2% (w/v). The concentration of the magnesium salt in the medium is preferably from 0.001 to 0.5%. (w/v), more preferably from 0.01 to 0.1% (w/v). The concentration of the zinc salt in the medium is preferably from 0.001 to 0.05% (w/v), more preferably from 0.005 to 0.05% (w/v).

The pH of medium (25° C.) is preferably from 3 to 7, more preferably from 3.5 to 6. The pH of the medium can be adjusted with bases such as calcium hydroxide, sodium hydroxide, calcium carbonate, and ammonia, or acids such as sulfuric acid and hydrochloric acid.

Preferred examples of the medium include a liquid medium containing from 7.5 to 30% carbon source, from 0.001 to 0.2% ammonium sulfate, from 0.01 to 0.6% potassium dihydrogen phosphate, from 0.01 to 0.1% magnesium sulfate heptahydrate, from 0.005 to 0.05% zinc sulfate heptahydrate, and from 3.75 to 20% calcium carbonate (wherein any concentration % is represented by % (w/v)).

To produce C4 dicarboxylic acid more efficiently using a transformed fungus obtained by using a filamentous fungus as a host, production may be carried out according to the following steps. That is, C4 dicarboxylic acids can be produced efficiently by preparing a spore suspension of a transformed cell (step A), culturing the spore suspension in a culture solution to germinate the spore to thereby prepare a mycelium (step B1), preferably further propagating the mycelium (step B2), and culturing the prepared mycelium to produce C4 dicarboxylic acids (step C). However, the step of culturing the transformed cell of the present invention is not limited to the following steps.

<Step A: Preparation of Spore Suspension>

A spore suspension can be prepared by inoculating spores of a transformed filamentous fungus into a medium, such as an inorganic agar medium (composition example: 2% glucose, 0.1% ammonium sulfate, 0.06% potassium dihydrogen phosphate, 0.025% magnesium sulfate heptahydrate, 0.009% zinc sulfate heptahydrate, 1.5% agar, wherein any concentration % is represented by % (w/v)) and PDA medium, and culturing stationarily at from 10 to 40° C., preferably from 27 to 30° C. for from 7 to 10 days to form a spore, and then suspending the spore in saline or the like. The spore suspension may contain a mycelium or not.

<Step B1: Preparation of Mycelium>

The spore suspension obtained in step A is inoculated into the culture solution and cultured to germinate the spore to obtain a mycelium. The number of spores of a filamentous fungus to be inoculated into a culture solution is from $1 \times 10^2$ to $1 \times 10^8$ spores/mL-culture solution, preferably from $1 \times 10^2$ to $5 \times 10^4$ spores/mL-culture solution, more preferably from $5 \times 10^2$ to $1 \times 10^4$ spores/mL-culture solution, further preferably from $1 \times 10^3$ to $1 \times 10^4$ spores/mL-culture solution. As the culture solution, commercially available medium, such as PDB medium, LB medium, NB medium, SB medium, and SD medium can be used. From the viewpoint of germinating rate and mycelium growth, the culture solution can be appropriately added with carbon sources including monosaccharides such as glucose and xylose, oligosaccharides such as sucrose, lactose and maltose, and polysaccharides such as starch; biological substances such as glycerin and citric acid; nitrogen sources such as ammonium sulfate, urea or amino acids; and other inorganic substances such as sodium, potassium, magnesium, zinc, iron, and various salts such as phosphate. The preferred concentration of monosaccharides, oligosaccharides, polysaccharides and glycerin is from 0.1 to 30% (w/v), the preferred concentration of citric acid is from 0.01 to 10% (w/v), the preferred concentration of ammonium sulfate, urea and amino acids is from 0.01 to 1% (w/v), and the preferred concentration of the inorganic substance is from 0.0001 to 0.5% (w/v). Into the culture solution, the spore suspension is inoculated, and the obtained solution is cultured for preferably from 24 to 120 hours, more preferably from 48 to 72 hours under the culture temperature control of from 25 to 42.5° C. while stirring at preferably from 80 to 250 rpm, more preferably from 100 to 170 rpm. The amount of the culture solution subjected to cultivation may be appropriately adjusted in accordance with the culture container, and may be about from 50 to 100 mL when the container is a 200 mL baffled flask, and about from 100 to 300 mL when the container is a 500 mL baffled flask. This culturing allows inoculated a spore to germinate and grow into a mycelium.

<Step B2: Propagation of Mycelium>

From the viewpoint of improving C4 dicarboxylic acid productivity, it is preferable to perform the step of further culturing the mycelium obtained in step B1 to propagate (step B2). The culture solution for propagation used in step B2 is not particularly limited and may be a commonly used inorganic culture solution containing glucose. Examples of the solution include a culture solution containing from 7.5 to 30% glucose, from 0.05 to 2% ammonium sulfate, from 0.03 to 0.6% potassium dihydrogen phosphate, from 0.01 to 0.1% magnesium sulfate heptahydrate, from 0.005 to 0.05% zinc sulfate heptahydrate, and from 3.75 to 20% calcium carbonate (herein any concentration % is represented by % (w/v)). The amount of culture solution is appropriately adjusted in accordance with the culture container, and for example, may be from 50 to 300 mL, preferably from 100 to 200 mL when the container is a 500 mL Erlenmeyer flask. Into the culture solution, the fungal cell cultured in step B1 is inoculated so as to obtain from 1 to 6 g-fungal cells/100 mL-culture solution, preferably from 3 to 4 g-fungal cells/100 mL-culture solution as wet weight, and the obtained solution is cultured for preferably from 12 to 120 hours, more preferably from 24 to 72 hours under the culture temperature control of from 25 to 42.5° C. while stirring at from 100 to 300 rpm, preferably from 170 to 230 rpm.

<Step C: Production of C4 Dicarboxylic Acid>

By culturing the mycelium of the filamentous fungus obtained in the above procedure (step B1 or B2), C4 dicarboxylic acids are produced by the fungus. Conditions of the cultivation may follow the ordinary culture conditions of a filamentous fungus described above. The amount of medium may be about from 20 to 80 mL when using a 200 mL Erlenmeyer flask, about from 50 to 200 mL when using a 500 mL Erlenmeyer flask, and when from 10 to 15 L when using a 30 L jar fermenter. The amount of medium may be appropriately adjusted in accordance with the culture container. The inoculation amount of the fungal cells obtained in step B1 or B2 to the medium is preferably from 5 g to 90 g-fungal cells/100 mL-medium, more preferably from 5 g to 50 g-fungal cells/100 mL-medium as wet weight. Suitably, the cell is cultured for from 2 to 240 hours, preferably from 12 to 120 hours under the temperature of from 25 to 45° C., while stirring at from 100 to 300 rpm, preferably from 150 to 230 rpm. When a jar fermenter is used, aeration is carried out preferably at from 0.05 to 2 vvm, more preferably at from 0.1 to 1.5 vvm.

The transformed cell of the present invention is cultured according to the above procedure to produce C4 dicarboxylic acids. After the cultivation, C4 dicarboxylic acids are recovered from the cultured broth. If necessary, the recovered C4 dicarboxylic acids may be further purified. Methods for recovering or purifying C4 dicarboxylic acids from the cultured broth are not particularly limited, and may be performed in accordance with known recovering or purifying methods. For example, C4 dicarboxylic acids in the cultured broth can be recovered or purified by removing the cell or the like from the cultured broth by gradient method, filtration, centrifugation or the like, concentrating the remaining culture as required, and then subjecting the concentrate to a crystallization method, ion exchange method, solvent extraction method, or combinations of these.

The transformed cell of the present invention isolated from cultured broth can be reused to produce C4 dicarboxylic acids. For example, to the transformed cell of the present invention isolated from the cultured broth, the medium described above is freshly added, and then the resultant is cultured again under the above conditions to produce C4 dicarboxylic acids. Thus, the produced C4 dicarboxylic acids can be recovered from the medium. This process can be further repeated. In the production method of the present invention, the cultivation of the transformed cell and the recovery of C4 dicarboxylic acids may be conducted in any one of batch mode, semi-batch mode, and continuous mode.

4. Exemplary Embodiment

As exemplary embodiments of the present invention, substances, production methods, uses and methods are further disclosed herein as follows. However, the present invention is not limited to these embodiments.

[1] A polypeptide consisting of the amino acid sequence represented by SEQ ID NO: 2 or an amino acid sequence having at least 90% identity therewith.

[2] The polypeptide according to [1], wherein preferably, the amino acid sequence having at least 90% identity with the amino acid sequence represented by SEQ ID NO: 2 is an amino acid sequence having 90% or more, preferably 95% or more, more preferably 96% or more, further preferably 97% or more, further preferably 98% or more, further preferably 99% identity with the amino acid sequence represented by SEQ ID NO: 2; or an amino acid sequence in which 1 or more and 10 or less, preferably 1 or more and 8 or less, more preferably 1 or more and 5 or less, further preferably 1 or more and 3 or less amino acids are deleted, substituted, added or inserted in the amino acid sequence represented by SEQ ID NO: 2.

[3] The polypeptide according to [1] or [2], preferably having carbonic anhydrase activity.

[4] The polypeptide according to any one of [1] to [3], preferably, having a function of improving C4 dicarboxylic acid productivity in a cell.

[5] The polypeptide according to [4], which improves the C4 dicarboxylic acid productivity in the cell by preferably 5% or more, more preferably 10% or more, further preferably 15% or more.

[6] A polynucleotide encoding the polypeptide according to any one of [1] to [5].

[7] The polynucleotide according to [6], preferably consisting of the nucleotide sequence represented by SEQ ID NO: 1 or a nucleotide sequence having at least 90% identity therewith.

[8] The polynucleotide according to [7], wherein preferably, the nucleotide sequence having at least 90% identity with the nucleotide sequence represented by SEQ ID NO: 1 is a nucleotide sequence having 90% or more, preferably 95% or more, more preferably 96% or more, further preferably 97% or more, further preferably 98% or more, further preferably 99% identity with the nucleotide sequence represented by SEQ ID NO: 1; or a nucleotide sequence in which 1 or more and 30 or less, preferably 1 or more and 24 or less, more preferably 1 or more and 15 or less, further preferably 1 or more and 9 or less nucleotides are deleted, substituted, added or inserted in the nucleotide sequence represented by SEQ ID NO: 1.

[9] The polynucleotide according to any one of [6] to [8], which is preferably cDNA or chemical synthetic DNA.

[10] A vector or DNA fragment comprising the polynucleotide according to any one of [6] to [9].

[11] The vector or DNA fragment according to [10], preferably further comprising a control region operably linked to the polynucleotide.

[12] A transformed cell comprising the exogenous polynucleotide according to any one of [6] to [9].

[13] A transformed cell preferably comprising the polynucleotide according to any one of [6] to [9] or the vector or DNA fragment according to [10].

[14] A transformed cell in which expression of the polynucleotide according to any one of [6] to [9] is enhanced.

[15] The transformed cell according to any one of [12], [13] or [14], which is preferably a cell of a microorganism.

[16] The transformed cell according to [15], wherein the microorganism is preferably a filamentous fungus.

[17] The transformed cell according to [16], wherein the filamentous fungus is preferably Rhizopus.

[18] The transformed cell according to [17], wherein the Rhizopus is preferably Rhizopus delemar or Rhizopus oryzae, more preferably Rhizopus delemar.

[19] The transformed cell according to any one of [12] to [18], which preferably has improved C4 dicarboxylic acid productivity.

[20] The transformed cell according to [19], which has improved C4 dicarboxylic acid productivity by preferably 5% or more, more preferably 10% or more, further preferably 15% or more.

[21] The transformed cell according to [19] or [20], wherein the C4 dicarboxylic acid is preferably fumaric acid, malic acid or succinic acid, more preferably fumaric acid or malic acid, further preferably fumaric acid.

[22] A method for producing a C4 dicarboxylic acid comprising culturing the transformed cell according to any one of [12] to [21].

[23] The method according to [22], further comprising recovering the C4 dicarboxylic acid from the cultured broth.

[24] The method according to [22] or [23], wherein the C4 dicarboxylic acid is fumaric acid, malic acid or succinic acid, more preferably fumaric acid or malic acid, further preferably fumaric acid.

[25] A method for producing a transformed cell comprising introducing the polynucleotide according to any one of [6] to [9] into a host cell, or enhancing expression of the polynucleotide according to any one of [6] to [9].

[26] A method for improving C4 dicarboxylic acid productivity in a host cell, comprising introducing the polynucleotide according to any one of [6] to [9] into the host cell, or enhancing expression of the polynucleotide according to any one of [6] to [9].

[27] The method according to [26], wherein the C4 dicarboxylic acid productivity in the host cell is improved by preferably 5% or more, more preferably 10% or more, further preferably 15% or more.

[28] The method according to [26] or [27], wherein the C4 dicarboxylic acid is preferably fumaric acid, malic acid or succinic acid, more preferably fumaric acid or malic acid, further preferably fumaric acid.

[29] The method according to any one of [25] to [28], preferably comprising introducing the vector or DNA fragment according to [10] into a host cell.

[30] The method according to any one of [25] to [29], wherein the host cell is preferably a cell of a microorganism.

[31] The method according to [30], wherein the microorganism is preferably a filamentous fungus.

[32] The method according to [31], wherein the filamentous fungus is preferably Rhizopus.

[33] The method according to [32], wherein the Rhizopus is preferably Rhizopus delemar or Rhizopus oryzae, more preferably Rhizopus delemar.

EXAMPLES

Hereinafter, the present invention will be described in more detail based on Examples, however, the present invention is not limited to these Examples.

Example 1 Preparation of Transformed Cell (1) Genome Extraction

Spores of Rhizopus delemar JCM (Japan Collection of Microorganisms/RIKEN) 5557 strain (hereinafter, referred to as 5557 strain) were inoculated into PDA medium, and cultured at 30° C. for 5 days. After culturing, the obtained mycelia were placed in a 3 mL homogenizing tube together with metal cones for a 3 mL tube (Yasui Kikai Corporation), and then immediately frozen in liquid nitrogen for 10 minutes or more. After that, the mycelia were homogenized for 10 seconds at 1700 rpm using a multi-beads shocker (Yasui Kikai Corporation). After homogenizing, 400 µL of TE Buffer (pH 8.0) (NIPPON GENE CO., LTD.) was added to the container and mixed by inversion, and 250 µL of the obtained mixture was transferred to 1.5 mL tube. From the resultant mycelium solution, genomic extraction was performed by using "Dr. GenTLE (from Yeast)" (Takara Bio Inc.) according to the Protocol. To 50 µL of the obtained genomic solution, 1 µL of RNase A (Roche, Ltd.) was added, and reacted at 37° C. for 1 hour. After the reaction, an equal amount of phenol chloroform was added and after mixing by tapping, the obtained mixture was centrifuged at 4° C. for 5 minutes at 14,500 rpm, and the supernatant was transferred to a fresh 1.5 mL tube. Again the phenol chloroform treatment was repeated and then the resultant was subjected to ethanol precipitation to obtain a purified genomic solution of 5557 strain.

(2) Preparation of cDNA (i) Extraction of Total RNA

Into 40 mL of liquid medium (0.1 g/L $(NH_4)_2SO_4$, 0.6 g/L $KH_2PO_4$, 0.25 g/L $MgSO_4.7H_2O$, 0.09 g/L $ZnSO_4.7H_2O$, 50 g/L calcium carbonate, and 100 g/L glucose), 6 g, in wet weight, of mycelia of 5557 strain was inoculated, and cultured at 35° C. for 8 hours at 170 rpm. The obtained culture solution was filtered to recover mycelia from the solution, and the mycelia were washed twice with 100 mL of 0.85% saline. After washing, excess water was removed by suction filtration, and then 0.3 g of the mycelia were weighed out, placed in a 3 mL homogenizing tube together with metal cones for a 3 mL tube (Yasui Kikai Corporation), and then immediately put into liquid nitrogen to freeze. The resulting frozen mycelia were homogenized for 10 seconds at 1,700 rpm using a multi-beads shocker (Yasui Kikai Corporation). To the homogenized mycelia, 500 µL of RLT buffer was added and mixed by inversion, then 450 µL of the obtained mixture was subjected to RNeasy Plant Mini Kit (Qiagen), and total RNA extraction was performed. To 40 µL of the obtained RNA solution, 1 µL of DNase I (Takara Bio Inc.) and 5 µL of 10×DNase I buffer (USB Corporation) were added. The obtained mixture was filled up to 50 µL with RNase free water and reacted at 37° C. for 30 minutes or more to remove residual DNA in the solution. Further, 1 µL of DNase I was added, the obtained mixture was reacted at 37° C. for 30 minutes, and the resultant was subjected to phenol/chloroform extraction followed by ethanol precipitation. The precipitate was dissolved in 50 μL of sterile water, and the concentration and purity of the RNA solution were determined using Qubit (Life Technologies). Further, the RNA solution was appropriately diluted, and the assay of the extracted RNA was performed using Agilent 2100 Bioanalyzer (Agilent Technologies) and RNA6000 Pico Kit (Agilent Technologies). The resultant RNA solution was confirmed to have an RNA degradation index, "RNA Integrity Number (RIN)" of 6.0 or more, and the resulting RNA solution was acquired as total RNA.

(ii) cDNA Synthesis cDNA synthesis was performed using SuperScript III First-Strand Synthesis SuperMix for qRT-PCR (Invitrogen). Specifically, 1 μg of the RNA solution obtained in (i) was filled up to 8 μL with DEPC water, after that, 10 μL of 2×RT Reaction Mix and 2 μL of RT Enzyme Mix were added to the solution and gently mixed, then the obtained mixture was reacted at 25° C. for 10 minutes, at 50° C. for 30 minutes, and at 85° C. for 5 minutes. After the reaction, 1 μL of RNase H was added to the solution, the obtained mixture was reacted at 37° C. for 20 minutes, and the resultant was used as cDNA solution.

(3) Preparation of Plasmid Vector (i) Introduction of trpC Gene Region to pUC18

Using the genomic DNA of 5557 strain obtained in (1) above as a template, a DNA fragment containing trpC gene (SEQ ID NO: 3) was synthesized by PCR using primers of oJK162 (SEQ ID NO: 4) and oJK163 (SEQ ID NO: 5). Then, using plasmid pUC18 as a template, a DNA fragment was amplified by PCR using primers oJK164 (SEQ ID NO: 6) and oJK165 (SEQ ID NO: 7). The above two fragments were ligated using In-Fusion HD Cloning Kit (Clontech Laboratories, Inc.) to construct a plasmid pUC18-trpC.

(ii) Cloning of ADH1 Promoter and Terminator

Using the genomic DNA of 5557 strain obtained in (1) above as a template, a DNA fragment containing a promoter sequence of ADH1 (SEQ ID NO: 8) and a DNA fragment containing a terminator sequence of ADH1 (SEQ ID NO: 9) each were amplified by PCR using a primer pair of oJK202 (SEQ ID NO: 10) and oJK204 (SEQ ID NO: 11), and a primer pair of oJK205 (SEQ ID NO: 12) and oJK216 (SEQ ID NO: 13) respectively. Next, using the plasmid pUCl8-tLpC obtained in (i) as a template, a DNA fragment was amplified by PCR using primers oJK210 (SEQ ID NO: 14) and oJK211 (SEQ ID NO: 15). The above three fragments were ligated in the same procedure as in (i) to construct a plasmid pUC18-trpC-Padh-Tadh. In the obtained plasmid, ADH1 promoter and terminator are arranged in this order in the downstream of trpC gene region. Further, in the downstream of ADH1 terminator, a Not I restriction enzyme recognition sequence is arranged.

(iii) Preparation of Plasmid Vector

A plasmid containing a gene represented by SEQ ID NO: 1 (hereinafter, referred to as RdCA1S) was synthesized by artificial gene synthesis, and amplified by PCR using primers NK-035 (SEQ ID NO: 16) and NK-036 (SEQ ID NO: 17). Next, using the plasmid pUC18-trpC-Padh-Tadh obtained in (ii) as a template, a DNA fragment was amplified by PCR using primers NK-011 (SEQ ID NO: 18) and NK-012 (SEQ ID NO: 19). The above two fragments were ligated in the same procedure as in (i) to construct a plasmid pUC18-trpC-Padh-RdCA1S-Tadh. In the obtained plasmid, the RdCA1S gene represented by SEQ ID NO: 1 was inserted between the ADH promoter and terminator. Further, a plasmid containing the gene represented by SEQ ID NO: 22 (hereinafter, referred to as RdCA1L) was synthesized by artificial gene synthesis, and amplified by PCR using primers Padh-RdCAfull F (SEQ ID NO: 24) and RdCA-Tadh R2 (SEQ ID NO: 25). Next, using the plasmid pUC18-trpC-Padh-Tadh obtained in (ii) as a template, a DNA fragment was amplified by PCR using primers RdPADH R (SEQ ID NO: 26) and RdTADH F (SEQ ID NO: 27). The above two fragments were ligated in the same procedure as in (i) to construct a plasmid pUC18-t pC-Padh-RdCA1L-Tadh.

The PCR primers used in preparation of plasmid vectors pUC18-trpC-Padh-RdCA1S-Tadh and pUC18-trpC-Padh-RdCA1L-Tadh are shown in Table 1.

TABLE 1

| Primer | Sequence (5'→3') | SEQ ID NO: |
|---|---|---|
| oJK162 | cgagctcgaattatttaaatgaa cagcaagttaataatctagaggg | 4 |
| oJK163 | tatgaccatgattacgatgagag gcaaaatgaagcgtac | 5 |
| oJK164 | atttaaataattcgagctcggta cccgggg | 6 |
| oJK165 | cgtaatcatggtcatagctg | 7 |
| oJK202 | tagagggaaaaagagagaattga aatagg | 10 |
| oJK204 | ttttgttatttaattgtattaat tgataatg | 11 |
| oJK205 | aattaaataacaaaatcatttta attacgcattttc | 12 |
| oJK216 | catgattacgcggccgcgccatt ataatgcactagtg | 13 |
| oJK210 | ctcttttccctctaatgagagg caaaatgaagcgtac | 14 |
| oJK211 | aattaaataacaaaaatgtcttc tatcgaaacctccaaaatctc | 15 |
| NK-035 | aattaaataacaaaaatggtgtc ttctcctatccg | 16 |
| NK-036 | gcgtaataaaatgattataaagg ttgacaagc | 17 |
| NK-011 | ttttgttatttaattgtattaat tg | 18 |
| NK-012 | tcattttaattacgcattttc | 19 |
| RdPADH R | ttttgttatttaattgtattaat tg | 24 |
| RdTADH F | tcattttaattacgcattttcat ttac | 25 |
| Padh-RdCAfull F | aattaaataacaaaaatgatgac ccaagaactggatg | 26 |
| RdCA-Tadh R2 | gcgtaataaaatgattataaagg ttgacaagcataaatag | 27 |

(4) Introduction of Gene into Host Cell (i) Preparation of Tryptophan Auxotrophic Strain A tryptophan auxotrophic strain which was used as a host cell of gene introduction was selected and acquired from the mutant strains obtained by ion beam irradiating to 5557 strains. Ion beam irradiation was carried out in ion irradiation facility of Takasaki Advanced Radiation Research Institute (TIARA: Takasaki Ion Accelerators for Advanced Radiation Application), of National Institutes for Quantum and Radiological Science and Technology. Irradiation was carried out by accelerating $^{12}C^{5+}$ using AVF cyclotron, and irradiating 100 to 1250 Gray with energy of 220 MeV. Spores were recovered from the irradiated mycelia, and among them, *Rhizopus delemar* 02T6 strain showing tryptophan auxotrophy (hereinafter referred to as 02T6 strain) was obtained. The 02T6 strain has a nucleotide sequence in which a nucleotide of $2093^{th}$ is deleted in trpC gene coding region (SEQ ID NO: 3) of full length 2298 bp.

(ii) Amplification of Plasmid Vector

Using the plasmid vectors pUC18-trpC-Padh-Tadh, pUC18-trpC-Padh-RdCA1S-Tadh and pUC18-trpC-Padh-RdCA1L-Tadh prepared in (3) above, *E. coli* DH5α strain (NIPPON GENE CO., LTD.) was transformed by competent cell transformation method. The obtained transformed cell was left to stand at 37° C. overnight, and the obtained colony was inoculated into 2 mL of LBamp liquid medium (Bacto Trypton 1%, Yeast Extract 0.5%, NaCl 1%, ampicillin sodium 50 μg/mL) and cultured at 37° C. overnight. From the obtained culture solution, each plasmid vector was purified using High Pure Plasmid Isolation Kit (Roche Life Science).

(iii) Introduction of Plasmid Vector into Host Cell

Each 10 μL of the DNA solutions (1 μg/μL) containing the plasmid vectors pUC18-trpC-Padh-Tadh, pUC18-trpC-Padh-RdCA1S-Tadh and pUC18-trpC-Padh-RdCA1L-Tadh obtained in (ii) was added to 100 μL of a gold particle solution (60 mg/mL) and mixed, then 40 μL of 0.1 M spermidine was added thereto, and the obtained mixture was stirred well with a vortex. Further 100 μL of 2.5 M $CaCl_2$ was added thereto, the obtained mixture was stirred well with a vortex for 1 minute and centrifuged for 30 seconds at 6,000 rpm, and the supernatant was removed. To the obtained precipitate, 200 μL of 70% EtOH was added, the obtained mixture was stirred with a vortex for 30 seconds and centrifuged for 30 seconds at 6,000 rpm, and the supernatant was removed. The obtained precipitate was resuspended in 100 μL of 100% EtOH.

Next, to spores of 02T6 strain prepared in (1), a gene was introduced by GDS-80 (Nepa Gene Co., Ltd.) using the above-described DNA-gold particle solution. The spores having the gene introduced were stationarily cultured in an inorganic agar medium (20 g/L glucose, 1 g/L ammonium sulfate, 0.6 g/L potassium dihydrogen.phosphate, 0.25 g/L magnesium sulfate.heptahydrate, 0.09 g/L zinc sulfatetheptahydrate, 15 g/L agar) at 30° C. for about a week. A part of the grown mycelia was scraped off with an inoculating loop, and suspended in TE (pH 8.0) (NIPPON GENE CO., LTD.). The obtained suspension was treated at 95° C. for 15 minutes and nucleic acids were extracted from the transformed strains. PCR reaction was carried out using the obtained nucleic acid as a template and primers oJK438 (SEQ ID NO: 20) and oJK439 (SEQ ID NO: 21), and the strain in which introduction of the DNA fragment of interest was confirmed was selected as a transformed strain. The PCR primers used are listed in Table 2. The obtained strain into which pUC18-trpC-Padh-RdCA1S-Tadh containing DNA where RdCA1S gene had been ligated in the downstream of ADH1 promoter was introduced was designated as CA1S strain, and the obtained strain into which pUC18-trpC-Padh-RdCA1L-Tadh containing DNA where RdCA1L gene had been ligated was introduced was designated as CA1L strain. Meanwhile, the obtained strain into which the plasmid vector pUC18-trpC-Padh-Tadh containing DNA where RdCA1 gene had not been inserted was introduced was used as negative control strain (hereinafter referred to as NC strain). The remaining mycelia were scraped off with an inoculating loop, and were vigorously mixed in the spore recovery solution (8.5 g/L sodium chloride, 0.5 g/L polyoxyethylene sorbitan monooleate). The mixed spore suspension was filtered with a 3GP100 cylindrical funnel glass filtration equipment (SIBATA SCIENTIFIC TECHNOLOGY Ltd.) to obtain a spore solution. The number of spores in the obtained spore solution was measured using TC20 Automated Cell Counter (Bio-Rad Laboratories, Inc.).

TABLE 2

| Primer | Sequence (5'→3') | SEQ ID NO: |
|---|---|---|
| oJK438 | gttccttgctgtggatttgtg | 20 |
| oJK439 | gggtgtatatctgtcctattcatg | 21 |

Example 2 Measurement of Intracellular Carbonic Anhydrase Activity of CA1 S Strain (1) Cultivation of Strain
(i) Preparation of Mycelia To a 500 mL baffled Erlenmeyer flask (AGC Inc.), 200 mL of SD/-Trp medium (Clontech Laboratories, Inc.) added with 0.5% (v/v) final concentration of sorbitan monolaurate (Rheodol SP-L10 (Kao Corporation)) and PDB medium (Becton, Dickinson and Company) were provided, and each of the spore solutions of CA1S strain and 5557 strain prepared in Example 1 was inoculated into the medium at a rate of $1\times10^3$ spores/mL-medium, and the obtained medium was cultured under stirring at 170 rpm at 27° C. for 3 days. The obtained cultured broth was filtered with a pre-sterilized stainless steel sieve having a 250 μm-mesh (AS ONE Corporation), and the mycelia were recovered on the filter.

(ii) Propagation of Mycelia

Into 100 mL of inorganic culture solution (0.1 g/L $(NH_4)_2SO_4$, 0.6 g/L $KH_2PO_4$, 0.25 g/L $MgSO_4.7H_2O$, 0.09 g/L $ZnSO_4.7H_2O$, 50 g/L calcium carbonate, and 100 g/L glucose) provided in a 500 mL Erlenmeyer flask, 5.0 to 8.0 g of wet mycelia recovered in (i) were inoculated and the obtained solution was cultured under stirring at 220 rpm at 27° C. for about 40 hours. The obtained cultured broth was filtered with previously sterilized stainless screen filter holder (MILLIPORE) to recover mycelia on the filter. Further the mycelia were washed on the filter holder with 200 mL of saline. The saline used for washing was removed by suction filtration.

(2) Preparation of Mycelial Homogenate

Into 40 mL of inorganic culture solution (0.0175 g/L $(NH_4)_2SO_4$, 0.06 g/L $KH_2PO_4$, 0.375 g/L $MgSO_4.7H_2O$, 0.135 g/L $ZnSO_4.7H_2O$, 50 g/L calcium carbonate, 100 g/L glucose) provided in 200 mL volume Erlenmeyer flask 6.0 g of wet mycelia of each CA1S strain and 5557 strain obtained in (1) above were inoculated, and the obtained solution was cultured under stirring at 170 rpm at 35° C. for 24 hours. The obtained cultured broth was filtered with previously sterilized stainless screen filter holder (MILLIPORE) to recover mycelia on the filter. Further the mycelia were washed on the filter holder with 200 mL of saline, and subjected to suction filtration for removing saline. The mycelia were frozen at −80° C. in 0.3 g each. The frozen mycelia were homogenized using a multi-beads shocker and metal cones (Yasui Kikai Corporation). To the resultant, 1 ml of 50 mM Tris-HCl buffer (pH 8.0) was added, and the mycelia were homogenized again and subjected to centrifugation at 4° C. for 5 minutes at 15,000 rpm, and then the obtained supernatant was concentrated and washed using AmiconUltra-0.5 (3 kDa) to obtain a mycelial homogenate.

(3) Measurement of Carbonic Anhydrase Activity

To the 96-well assay plate (IWAKI CO., LTD.) in which 10 µL of the mycelial homogenate of CA1S strain and 5557 strain obtained in (2) above were added, 120 µL of a reaction solution (50 mM final concentration of Tris-HCl pH 8.0, 50 mM $Na_2SO_4$, 0.004% phenol red) was added, and then 70 µL of $CO_2$ saturated water obtained by immersing dry ice into water for 30 minutes was added to initiate a reaction. By using the time until the absorbance at 557 nm at 30° C. becomes lower than 0.35 as a standard, the activity value (U/g wet weight of the mycelia) was calculated in accordance with the document (C. S. Gai et al., AMB Express 2014, 4, 2-13). The analysis results are shown in Table 3. Compared to the carbonic anhydrase activity of 5557 strain which is a wild-type strain, the carbonic anhydrase activity of CA1S strain was improved 22 folds.

TABLE 3

| Sample | Carbonic anhydrase activity (U/g wet weight of mycelia) | Relative comparison |
|---|---|---|
| 5557 strain | 5.1 | 1 |
| CA1S strain | 112 | 22 |

Example 3 C4 Dicarboxylic Acid Productivity of CA1S Strain and CA1L Strain (1) Cultivation of strain
(i) Preparation of Mycelia To a 500 mL baffled Erlenmeyer flask (AGC Inc.), 200 mL of SD/−Trp medium (Clontech Laboratories, Inc.) added with 0.5% (v/v) final concentration of sorbitan monolaurate (Rheodol SP-L10 (Kao Corporation)) was provided, and each of the spore solutions of CA1S strain, CA1L strain and NC strain prepared in Example 1 was inoculated to the medium at a rate of $1 \times 10^3$ spores/mL-medium, and the obtained solution was cultured under stirring at 170 rpm at 27° C. for 3 days. The obtained cultured broth was filtered with a pre-sterilized stainless steel sieve having a 250 µm-mesh (AS ONE Corporation), and the mycelia were recovered on the filter.

To a 500 mL baffled Erlenmeyer flask (AGC Inc.), 200 mL of SD/−Trp medium (Clontech Laboratories, Inc.) added with 0.5% (v/v) final concentration of sorbitan monolaurate (Rheodol SP-L10 (Kao Corporation)) was provided, and each of the spore solutions of CA1 strains and NC strain prepared in Example 1 was inoculated to the medium at a rate of $1 \times 10^3$ spores/mL-medium, and the obtained solution was cultured under stirring at 170 rpm at 27° C. for three days. The obtained cultured broth was filtered with a pre-sterilized stainless steel sieve having a 250 µm-mesh (AS ONE Corporation), and the mycelia were recovered on the filter.

(ii) Propagation of Mycelia

The mycelia were propagated under the same conditions as in Example 2(1)(ii).

(2) Evaluation of C4 Dicarboxylic Acid Productivity of Transformed Strains

Into 40 mL of inorganic culture solution (0.0175 g/L $(NH_4)_2SO_4$, 0.06 g/L $KH_2PO_4$, 0.375 g/L $MgSO_4.7H_2O$, 0.135 g/L $ZnSO_4.7H_2O$, 50 g/L calcium carbonate, 100 g/L glucose) provided in a 200 mL Erlenmeyer flask, 6.0 g of wet mycelia of each CA1S strain, CA1L strain and NC strain obtained in (1) above each were inoculated, and the obtained solution was cultured under stirring at 170 rpm at 35° C. After cultivation for 8 hours, the culture supernatant having no mycelia were recovered, and subjected to quantification of C4 dicarboxylic acid (fumaric acid, malic acid) by using the procedure described in Reference Example 1 below. Based on the quantified amount of each C4 dicarboxylic acid, improvement rates of each C4 dicarboxylic acid productivity of CA1S strain and CA1L strain were calculated according to the following equation.

Improvement rate (%)=(production speed of CA1S strain and CA1L strain/production speed of NC strain and 5557 strain)×100−100

The results are shown in Table 5. It is observed that as compared to the NC strain into which RdCA1 gene was not introduced, CA1S strain has improved productivities of malic acid by 18% and of fumaric acid by 28%. On the other hand, no improvement in fumaric acid productivity was observed in CA1L strain as compared to 5557 strain.

TABLE 4

| Strain Name | Malic acid | Fumaric acid |
|---|---|---|
| Production speed of C4 dicarboxylic acid at 8-hour (g/L/h) | | |
| CA1S strain | 0.13 | 1.92 |
| NC strain | 0.11 | 1.50 |
| Production speed of C4 dicarboxylic acid at 19-hour (g/L/h) | | |
| CA1L strain | 0.24 | 0.93 |
| 5557 strain | 0.07 | 1.26 |

TABLE 5

| | Improvement rates of productivity (%) | |
|---|---|---|
| Strain Name | Malic acid | Fumaric acid |
| CA1S strain | 18 | 28 |
| CA1L strain | 343 | −26 |

Reference Example 1 Quantification of C4 Dicarboxylic Acid

Quantification of C4 dicarboxylic acid (fumaric acid, malic acid and succinic acid) in the culture supernatant was performed by HPLC.

The culture supernatant to be subjected to HPLC analysis was diluted appropriately in advance using 37 mM sulfuric acid, and insoluble matters were removed using DISMIC-13cp (0.20 µm cellulose acetate membrane, ADVANTEC) or AcroPrep 96 filter plates (0.2 µm GHP membranes, Pall Corporation).

As the device for HPLC, the LaChrom Elite was used (Hitachi High-Technologies Corporation). As the analytical column, a polymer column for organic acid analysis ICSep ICE-ION-300 (7.8 mm I.D.×30 cm, TRANSGENOMIC) connected to ICSep ICE-ION-300 Guard Column Cartridge (4.0 mm I.D.×2.0 cm, TRANSGENOMIC) was used. Elution was conducted using 10 mM sulfuric acid as the eluent under conditions of flow rate of 0.5 mL/min and column temperature of 50° C. Each C4 dicarboxylic acid was detected by using a UV detector (detection wavelength of 210 nm). The concentration calibration curves were prepared using standard samples [fumaric acid (vendor code: 063-00655, Wako pure chemical industries), malic acid (vendor code: 135-00562, Wako pure chemical industries)

and succinic acid (vendor code 194-04335, Wako pure chemical industries)]. Based on the respective concentration calibration curve, quantification of each component was performed.

The value obtained by subtracting the initial amount of C4 dicarboxylic acid in the medium from the amount of C4 dicarboxylic acid in the medium used for quantification was set as a production amount of C4 dicarboxylic acid. The values obtained by dividing the amount of each C4 dicarboxylic acid at 8-hour after the start of cultivation by the culture time were used as the production speed of each C4 dicarboxylic acid of the cell for calculation.

What is claimed is:

1. A transformed cell comprising a polynucleotide encoding a polypeptide, the amino acid sequence of the polypeptide consisting of the amino acid sequence of SEQ ID NO: 2 or an amino acid sequence having at least 90% identity therewith and having carbonic anhydrase activity, wherein the polynucleotide is exogenous to the cell.

2. The transformed cell according to claim 1, wherein the cell has improved C4 dicarboxylic acid productivity.

3. The transformed cell according to claim 2, wherein the cell has improved C4 dicarboxylic acid productivity by 5% or more.

4. The transformed cell according to claim 2, wherein the C4 dicarboxylic acid is fumaric acid, malic acid, or succinic acid.

5. A transformed cell wherein expression of a polynucleotide is enhanced, wherein the polynucleotide encodes a polypeptide consisting of the amino acid sequence represented by SEQ ID NO: 2 or an amino acid sequence having at least 90% identity therewith and having carbonic anhydrase activity.

6. The transformed cell according to claim 5, wherein the cell has improved C4 dicarboxylic acid productivity.

7. The transformed cell according to claim 5, wherein the cell has improved C4 dicarboxylic acid productivity by 5% or more.

8. The transformed cell according to claim 5, wherein the C4 dicarboxylic acid is fumaric acid, malic acid, or succinic acid.

9. A method for producing C4 dicarboxylic acid comprising culturing the transformed cell according to claim 1.

10. The method according to claim 9, further comprising recovering the C4 dicarboxylic acid from the cultured broth.

11. The method according to claim 9, wherein the C4 dicarboxylic acid is fumaric acid, malic acid or succinic acid.

12. A method for improving C4 dicarboxylic acid productivity in a host cell, comprising introducing, into the host cell, a polynucleotide that encodes a polypeptide, the amino acid sequence of the polypeptide consisting of the amino acid sequence of SEQ ID NO: 2 or an amino acid sequence having at least 90% identity therewith and having carbonic anhydrase activity, or enhancing expression of the polynucleotide in the host cell.

13. The method according to claim 12, wherein the C4 dicarboxylic acid productivity in the host cell is improved by 5% or more.

14. The method according to claim 12, wherein the C4 dicarboxylic acid is fumaric acid, malic acid or succinic acid.

15. A method for producing a C4 dicarboxylic acid comprising culturing the transformed cell according to claim 5.

16. The method according to claim 15, further comprising recovering the C4 dicarboxylic acid from the cultured broth.

17. The method according to claim 15, wherein the C4 dicarboxylic acid is fumaric acid, malic acid or succinic acid.

18. A method for improving C4 dicarboxylic acid productivity in a host cell, comprising enhancing expression of a polynucleotide, wherein the polynucleotide encodes a polypeptide consisting of the amino acid sequence of SEQ ID NO: 2 or an amino acid sequence having at least 90% identity therewith and having carbonic anhydrase activity.

19. The method according to claim 18, wherein the C4 dicarboxylic acid productivity in the host cell is improved by 5% or more.

20. The method according to claim 18, wherein the C4 dicarboxylic acid is fumaric acid, malic acid, or succinic acid.

* * * * *

SEQUENCE LISTING

<160> NUMBER OF SEQ ID NOS: 27

<210> SEQ ID NO 1
<211> LENGTH: 678
<212> TYPE: DNA
<213> ORGANISM: Rhizopus delemar

<400> SEQUENCE: 1

```
atggtgtctt ctcctatccg aatcaataag tttgatccca aagatgaaaa acttgatagt      60
ttattaaaga gtaacgctga atggtccaag gccgtgacag aagctgaccc caactttttc     120
aaaaagctgg ctcagattca agaacccaag atcttgtggg ttggctgtgc tgattctcgt     180
gtgcctgcta atcaactggt tcaattggca ccgggtgaag tctttgttca cagaaatatc     240
gcgaatgtcg tctgtcactc tgatttgaat tgcctttctg tcttacaata tgcggtagat     300
gtgctcaagg tagagcacgt gattgtctgc ggtcactcca actgtggtgg tgtggcagct     360
gcgatgggca gtggtcaata tggtctgatt gataattggc ttaggaacat caaggatgtc     420
tatagatttt atgaaaagga actggatgaa atcaaggatt caaggaacg tctgagtcga     480 ctgatcgaat taacgcgat acactctgct caaaatgtat gccgttcgac gattgttcag     540
aacgcatggc atcgtggaca gaaattgaca gtacacgcat gggtttatga cttggaaaat     600
ggattggtaa agagattgga attcagccat aaagatcctg ctaaacttcc atctattat      660 gcttgtcaac ctttataa                                                    678
```

<210> SEQ ID NO 2
<211> LENGTH: 225
<212> TYPE: PRT
<213> ORGANISM: Rhizopus delemar

<400> SEQUENCE: 2

```
Met Val Ser Ser Pro Ile Arg Ile Asn Lys Phe Asp Pro Lys Asp Glu
1               5                   10                  15

Lys Leu Asp Ser Leu Leu Lys Ser Asn Ala Glu Trp Ser Lys Ala Val
            20                  25                  30

Thr Glu Ala Asp Pro Asn Phe Phe Lys Lys Leu Ala Gln Ile Gln Glu
        35                  40                  45

Pro Lys Ile Leu Trp Val Gly Cys Ala Asp Ser Arg Val Pro Ala Asn
    50                  55                  60

Gln Leu Val Gln Leu Ala Pro Gly Glu Val Phe Val His Arg Asn Ile
65                  70                  75                  80

Ala Asn Val Val Cys His Ser Asp Leu Asn Cys Leu Ser Val Leu Gln
                85                  90                  95

Tyr Ala Val Asp Val Leu Lys Val Glu His Val Ile Val Cys Gly His
            100                 105                 110

Ser Asn Cys Gly Gly Val Ala Ala Ala Met Gly Ser Gly Gln Tyr Gly
        115                 120                 125

Leu Ile Asp Asn Trp Leu Arg Asn Ile Lys Asp Val Tyr Arg Phe Tyr
    130                 135                 140

Glu Lys Glu Leu Asp Glu Ile Lys Asp Ser Lys Glu Arg Leu Ser Arg
145                 150                 155                 160
```

Leu Ile Glu Phe Asn Ala Ile His Ser Ala Gln Asn Val Cys Arg Ser
            165                 170                 175

Thr Ile Val Gln Asn Ala Trp His Arg Gly Gln Lys Leu Thr Val His
            180                 185                 190

Ala Trp Val Tyr Asp Leu Glu Asn Gly Leu Val Lys Arg Leu Glu Phe
        195                 200                 205

Ser His Lys Asp Pro Ala Lys Leu Pro Ser Ile Tyr Ala Cys Gln Pro
    210                 215                 220

Leu
225

<210> SEQ ID NO 3
<211> LENGTH: 2298
<212> TYPE: DNA
<213> ORGANISM: Rhizopus delemar

<400> SEQUENCE: 3

| | | | | | |
|---|---|---|---|---|---|
| atgaccactt | tacttattga | caactacgac | agttttactt | ataatgtcta | tcaatacttg | 60 |
| agctgccaag | gcgccaatgt | agttgtctac | agaaacgaca | aaatcaccat | ttccgaaatt | 120 |
| gagcaattgg | ctcctcgcaa | tattgtcatc | tcacctggcc | ctggccaccc | ttccaccgat | 180 |
| gccggtgtct | ctcgagaggc | cattcgagct | tttgcaggaa | agattcccat | cttgggtatt | 240 |
| tgtatgggtc | agcaatgtat | gtatgaagtg | tacggtggta | agtgtcata | tgcaggtgat | 300 |
| attgtgcatg | gcaaggcatc | cagcatcaag | catgacagtc | gaggtatctt | caagggcgtt | 360 |
| cctcaaaaca | catggtcac | tcgttaccat | tcccttgctg | gcatgccttc | tactttacct | 420 |
| gaaacattag | aagtcactgc | gactaccgac | gatggtatca | tcatgggcat | tcgacacaag | 480 |
| gaatacactg | tcgaaggtgt | tcagttccat | cctgaaagta | tcctttgtga | acacggacat | 540 |
| acgatgatca | acaacttctt | aagcttgcgt | ggtggcacct | gggaagagaa | tcctgcagcc | 600 |
| ggtgttgtct | ttaagaaagc | tcgttccgaa | acacccaaaa | tcagtgctag | tgaatcccaa | 660 |
| ctcgatctct | ctcagcaaca | acctgccgca | gcaccttcca | tcttgacccg | catttactct | 720 |
| caacgactca | aggatgttca | ggcagccaag | gagattcccg | ccagacatt | tgaagattta | 780 |
| gaaaaacttt | taaagttgca | cgtcgcccca | cctcttcaag | acgtcgtcgc | tcgcgtgcgt | 840 |
| caaagcaagc | ccgccttgat | ggccgaagtc | aagcgtgcct | ctccctcgaa | aggaaacatt | 900 |
| gatgtttcgg | ccaacgcggc | tgagcaggca | cttcaatatg | ctttagcagg | tgcaagcgtc | 960 |
| gtctctgttc | tgactgaacc | caaatggttc | cgcggtacga | ttcatgatat | gcatcaggtc | 1020 |
| cgagaggcct | tgagccatct | gcccaaccgt | ccttgtgtgt | tgagaaagga | ttttattgtc | 1080 |
| gatcgctatc | aaatcttgga | aggttgtctg | tacggtgctg | atactatctt | gttgatcgtg | 1140 |
| gccatgctga | atgatgaaca | actgcacgaa | ttgtatcact | atgcgaaatc | attaggtatg | 1200 |
| gaacccttgg | tcgaagtcaa | taatacgaa | gagatggccc | gtgccaatgc | tttgggcgca | 1260 |
| cgtctggtgg | gtgttaataa | tcgcaacttg | cacagctttg | atgttgatat | ggaaccacg | 1320 |
| agtcgattgg | tagagatggt | gcctgaagga | acgatcttgt | gtgcactttc | tggtattact | 1380 |
| ggacgagctg | atgttgaaat | gtacgtcaaa | cagggtgtgc | acgctgtctt | ggtgggtgaa | 1440 |
| gccctgatgc | gtgcttggaa | tttgaaggag | tttgtgtctg | atttgttggg | tcatgaaaag | 1500 |
| aaggatcctg | tgcctgtgtc | caaggaatca | aaatcttcac | tagtcaaggt | atgtggtatc | 1560 |
| tctagtgtgg | atgcagcagt | tgaagcagcc | aagtcagggg | ctgacttgat | tggtcttatc | 1620 |
| tttgctgaaa | agtccaaacg | aaaagtgtct | ttggaaagag | ctcaagaaat | cgtgtcctca | 1680 |

```
gtgcgtgcgt tggatattca agtcaaacga acgttatcaa atgatgattc tcaactggat    1740
tggttccaga tgcacaagcg tctcttggaa aagcgagcaa gaaaaccttt ggtagttggc    1800
gtgtttgtga atcaatcgat tgaatacatg actgaggtgg caacgacagt cggactggac    1860
cttattcagc tgcatggaac cgaatcaacg gagcttgcac gctatttacc cgtgcctgtc    1920
atcaaagctt tccatatcga cagtggtgag ttcaatgaag ctcagatacc aaacctaaat    1980
caaccaggct cttatcatta tgtcttactg gacgctaaag tgcccagctt accatcggat    2040
caacaaggtg gacgtggtgt caagtttgat tggtcaattg ctaccaaaat cgtgaaacat    2100
aggcactttg agttttttggg taatcaagat ttccctgtca tcttggctgg tgggttggat    2160
cctaccaatg tggcatctgc cattcaacag gtgaaaccct ggattgtgga tgtgtcgagt    2220
ggtgttgaaa cagatggagt gaaggattta gaaaagattc gtgcctttgt taaaactgtc    2280
cagtcaacac aattttaa                                                  2298

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 4
cgagctcgaa ttatttaaat gaacagcaag ttaataatct agaggg                   46

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
tatgaccatg attacgatga gaggcaaaat gaagcgtac                           39

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
atttaaataa ttcgagctcg gtacccgggg                                     30

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cgtaatcatg gtcatagctg                                                20

<210> SEQ ID NO 8
<211> LENGTH: 1000
<212> TYPE: DNA
<213> ORGANISM: Rhizopus delemar

<400> SEQUENCE: 8
```

```
tagagggaaa aagagagaat tgaaatagga gaggatgagt caaaatatag tttacataaa    60
atttctcttt tttgtgttaa atataatcta atagcagggg ttttcttagt ttacgtttat   120
atcaaagtta tcaagcatac actttttat gattttcat actttaatcc cttttagtat    180
tctattgttt gaaaggagag aaaaaacagc tgagggtacg gtgcacacga gatcttacga   240
taattttcct gcccaacagg aaagaagtaa ttgatcttga ttgacgctcg gagtttgcac   300
gttcggagtt tgcacttcac attgagttat actcttactt attttgaagg aagggacgag   360
aaaagatgta aatataataa taacagtagt aaatagtatg cgcatcaaga acagctacca   420
acaaaagaga gaaatatgag cttaataatg aacaatgtaa atggcagaat gaaatttaat   480
tatcaaagcg gcatctttca gaccttccgt tacttccgat agagttttt atgcaaagta    540 ataacaactg tatatataaa aaaagaagg ttatcaagca aaagccacaa tgtcatatct    600
ggaataatca agagtaacta ttgaatgttg gtagccaaaa gaggcacgta atttatgac    660 gaaatatcac acaaaaagat tattttgaca attcatgaat aggacagaga tacaccctaa   720
acatgaaatg taagctatat ttaaacacct caagttaatt ttgaagcttc atttgtatta   780
ttgtaaccat ttagacaagc taaatccttt ttattattgt ccttattgat tttatccaga   840
ttaccgtatc taaagagcga tcaacagaaa aacggctgat tttagaccaa agtttcacaa   900
actacatttg catgaacgtc atatatatat aaaccttgac ttttcttttt tttttttttt   960
tttttttttc attatcaatt aatacaatta ataacaaaa                        1000

<210> SEQ ID NO 9
<211> LENGTH: 634
<212> TYPE: DNA
<213> ORGANISM: Rhizopus delemar

<400> SEQUENCE: 9
tcattttaat tacgcatttt catttactaa tttgttacat tttgataacg tcaataaatc    60
ttctaatttc ttttgttctc aaacagttta cagttctatc ttttttttta ccacaatcaa   120
ttctcaatat acaacatagc aaatgtgctt cagtaaattc attaaattct tttaaaaaaa   180
ggtaatttgt agcataaaat tcgactttat tgacgttttt tttatgatca tatacaaata   240
aaatagttgc gaatgagaac taaatttttc attgttttta gtcatatcat ctggctgttg   300
cacgatgatc gcagcatatt tttcttcaca acactcatcc tataagcacc tttcaggact   360
ttcgtctgca ctttccatat ttgatttcat caattgattt gaattttat ccagtacaat    420 ggtttgaatc tatacaataa attagtcaca gtataaaatt atgtctcatc ttgaacacac   480
acctgcttaa caaagaaatg aagcactcta tcaatagtaa atacaatata tgcatcgatg   540
ccaaatatat atcgtacatt ctcttcaaac gtagcttgat ctaaatcgcc atcaataaac   600
ctttcaatca tcctcactag tgcattataa tggc                              634

<210> SEQ ID NO 10
<211> LENGTH: 29
<212> TYPE: DNA
<213> ORGANISM: Artificial
<220> FEATURE:
<223> OTHER INFORMATION: Synthetic oligonucleotide

<400> SEQUENCE: 10
tagagggaaa agagagaat tgaaatagg                                      29

<210> SEQ ID NO 11
<211> LENGTH: 31
```

```
<212> TYPE: DNA
<213> ORGANISM: Artificial Sequence
<220> FEATURE:
<223> OTHER INFORMATION: Synthetic oligonucleotide

<400> SEQUENCE: 11
ttttgttatt taattgtatt aattgataat g                                    31

<210> SEQ ID NO 12
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 12
aattaaataa caaaatcatt ttaattacgc attttc                               36

<210> SEQ ID NO 13
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 13
catgattacg cggccgcgcc attataatgc actagtg                              37

<210> SEQ ID NO 14
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 14 ctcttttcc ctctaatgag aggcaaaatg aagcgtac                              38

<210> SEQ ID NO 15
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 15
aattaaataa caaaaatgtc ttctatcgaa acctccaaaa tctc                      44

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
aattaaataa caaaaatggt gtcttctcct atccg                                35

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 17
```

```
gcgtaattaa aatgattata aaggttgaca agc                                    33

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ttttgttatt taattgtatt aattg                                             25

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
tcattttaat tacgcatttt c                                                 21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
gttccttgct gtggatttgt g                                                 21

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
gggtgtatct ctgtcctatt catg                                              24

<210> SEQ ID NO 22
<211> LENGTH: 1128
<212> TYPE: DNA
<213> ORGANISM: Rhizopus delemar

<400> SEQUENCE: 22
atgatgaccc aagaactgga tgatgaacca ctgtcactgg tgatagtcaa gaatgatgaa        60
caagtgatag caggatcaca aagtggtgct ttgtatacct ggaattggaa cacatggtca       120
gattactcaa aatggatagg tcatcctaat tcagtggatg ctctttgcaa gttggatgag       180
gacacgatct gtaccggagg cagtgatggg ttactgcgat tgatcactgt atcaccacag       240
cagcaattcg aaggtatcct gggtgatcac ggtgaggatt cccgataga gaagatggcg        300 gttggttttg atgaaaagta cctggcaagt tgtgggcatg atttacattt acgcttttgg       360
aacatcgaat tctttatga aaacacaaag cggaaacaac aagaaacagc gacatctggt        420
gtaaataaac aagaaactaa tgaacccaac acagtgtctt ctcctatccg aatcaataag       480
tttgatccca aagatgaaaa acttgatagt ttattaaaga gtaacgctga atggtccaag       540
gccgtgacag aagctgaccc caacttttc aaaaagctgg ctcagattca agaacccaag        600
atcttgtggg ttggctgtgc tgattctcgt gtgcctgcta atcaactggt tcaattggca       660
```

```
ccgggtgaag tctttgttca cagaaatatc gcgaatgtcg tctgtcactc tgatttgaat    720
tgcctttctg tcttacaata tgcggtagat gtgctcaagg tagagcacgt gattgtctgc    780
ggtcactcca actgtggtgg tgtggcagct gcgatgggca gtggtcaata tggtctgatt    840
gataattggc ttaggaacat caaggatgtc tatagatttt atgaaaagga actggatgaa    900
atcaaggatt caaggaacg tctgagtcga ctgatcgaat taacgcgat acactctgct    960 caaaatgtat gccgttcgac gattgttcag aacgcatggc atcgtggaca gaaattgaca    1020
gtacacgcat gggtttatga cttggaaaat ggattggtaa agagattgga attcagccat    1080
aaagatcctg ctaaacttcc atctatttat gcttgtcaac ctttataa                 1128
```

<210> SEQ ID NO 23
<211> LENGTH: 375
<212> TYPE: PRT
<213> ORGANISM: Rhizopus delemar

<400> SEQUENCE: 23

```
Met Met Thr Gln Glu Leu Asp Asp Glu Pro Leu Ser Leu Val Ile Val
1               5                   10                  15

Lys Asn Asp Glu Gln Val Ile Ala Gly Ser Gln Ser Gly Ala Leu Tyr
                20                  25                  30

Thr Trp Asn Trp Asn Thr Trp Ser Asp Tyr Ser Lys Trp Ile Gly His
            35                  40                  45

Pro Asn Ser Val Asp Ala Leu Cys Lys Leu Asp Glu Asp Thr Ile Cys
        50                  55                  60

Thr Gly Gly Ser Asp Gly Leu Leu Arg Leu Ile Thr Val Ser Pro Gln
65                  70                  75                  80

Gln Gln Phe Glu Gly Ile Leu Gly Asp His Gly Glu Asp Phe Pro Ile
                85                  90                  95

Glu Lys Met Ala Val Gly Phe Asp Glu Lys Tyr Leu Ala Ser Cys Gly
            100                 105                 110

His Asp Leu His Leu Arg Phe Trp Asn Ile Glu Phe Leu Tyr Glu Asn
        115                 120                 125

Thr Lys Arg Lys Gln Gln Glu Thr Ala Thr Ser Gly Val Asn Lys Gln
    130                 135                 140

Glu Thr Asn Glu Pro Asn Thr Val Ser Ser Pro Ile Arg Ile Asn Lys
145                 150                 155                 160

Phe Asp Pro Lys Asp Glu Lys Leu Asp Ser Leu Leu Lys Ser Asn Ala
                165                 170                 175

Glu Trp Ser Lys Ala Val Thr Glu Ala Asp Pro Asn Phe Phe Lys Lys
            180                 185                 190

Leu Ala Gln Ile Gln Glu Pro Lys Ile Leu Trp Val Gly Cys Ala Asp
        195                 200                 205

Ser Arg Val Pro Ala Asn Gln Leu Val Gln Leu Ala Pro Gly Glu Val
    210                 215                 220

Phe Val His Arg Asn Ile Ala Asn Val Cys His Ser Asp Leu Asn
225                 230                 235                 240

Cys Leu Ser Val Leu Gln Tyr Ala Val Asp Val Leu Lys Val Glu His
                245                 250                 255

Val Ile Val Cys Gly His Ser Asn Cys Gly Val Ala Ala Ala Met
            260                 265                 270

Gly Ser Gly Gln Tyr Gly Leu Ile Asp Asn Trp Leu Arg Asn Ile Lys
        275                 280                 285
```

```
Asp Val Tyr Arg Phe Tyr Glu Lys Glu Leu Asp Glu Ile Lys Asp Ser
    290                 295                 300

Lys Glu Arg Leu Ser Arg Leu Ile Glu Phe Asn Ala Ile His Ser Ala
305                 310                 315                 320

Gln Asn Val Cys Arg Ser Thr Ile Val Gln Asn Ala Trp His Arg Gly
                325                 330                 335

Gln Lys Leu Thr Val His Ala Trp Val Tyr Asp Leu Glu Asn Gly Leu
            340                 345                 350

Val Lys Arg Leu Glu Phe Ser His Lys Asp Pro Ala Lys Leu Pro Ser
        355                 360                 365

Ile Tyr Ala Cys Gln Pro Leu
    370                 375

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
ttttgttatt taattgtatt aattg                                           25

<210> SEQ ID NO 25
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 25
tcattttaat tacgcatttt catttac                                         27

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 26
aattaaataa caaaaatgat gacccaagaa ctggatg                              37

<210> SEQ ID NO 27
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 27
gcgtaattaa aatgattata aaggttgaca agcataaata g                         41
```